United States Patent

Pozzoli et al.

[11] Patent Number: 5,840,964
[45] Date of Patent: Nov. 24, 1998

[54] PROCESS FOR THE PREPARATION OF THE ENANTIOMERS OF 2-(2-FLUORO-4-BIPHENYL)PROPIONIC ACID

[75] Inventors: Claudio Pozzoli, Monza; Graziano Castaldi, Briona, both of Italy

[73] Assignee: Zambon Group S.P.A., Vicenza, Italy

[21] Appl. No.: 577,377

[22] Filed: Dec. 22, 1995

[30] Foreign Application Priority Data

Dec. 27, 1994 [IT] Italy .................................. MI94A2647

[51] Int. Cl.⁶ ............................. C07B 57/00; C07B 55/00
[52] U.S. Cl. ........................... 562/401; 562/402; 549/371
[58] Field of Search ..................... 562/401, 402

[56] References Cited

U.S. PATENT DOCUMENTS

| | | | |
|---|---|---|---|
| 4,209,638 | 6/1980 | Nicholson et al. | 562/401 |
| 4,622,419 | 11/1986 | Cannata et al. | 562/401 |
| 4,625,054 | 11/1986 | Bernini | 562/401 |
| 4,973,745 | 11/1990 | Blaschke et al. | 562/401 |
| 4,983,765 | 1/1991 | Lukas | 562/401 |
| 5,202,484 | 4/1993 | Villa et al. | 564/302 |

FOREIGN PATENT DOCUMENTS

| | | |
|---|---|---|
| 0143371 | 11/1984 | European Pat. Off. . |
| 0182279 | 11/1986 | European Pat. Off. . |
| 9204018 | 3/1992 | WIPO . |

OTHER PUBLICATIONS

The Merck Index, 11th Edition, Merck & Co., Inc., 1989, p. 657.

"Crystallization–Induced Aymmetric transformations," *Enantiomers, Racemates, and Resolutions*, Jean Jacques, Andre Collet, Samuel Wilen, 1981, pp. 369–377.

"Enantiomeric separation of chiral carboxylic acids, as their diastereomeric carboxamides, by a thin–layer chromatography," P. Slegel, G. Vereczkey–Donath, L. Ladanyi and M. Toth–Lauritz, *Journal of Pharmaceutical & Biomedical Analysis*, vol. 5, No. 7, pp. 665–673, 1987.

*Primary Examiner*—Johann Richter
*Assistant Examiner*—Laura L. Stockton

[57] ABSTRACT

A process for the preparation of 2-(2-fluoro-4-biphenyl) propianic acid enantiomers comprising a II order resolution of ketals of formula

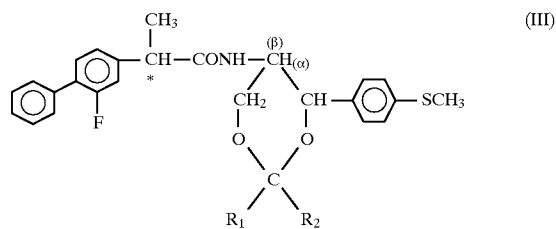

wherein $R_1$ ad $R_2$ have the meanings reported in the description; the asterisk shows the chiral carbon atom and the asymmetric carbon atoms marked by α and β have both R or S configuration is described.

14 Claims, No Drawings

PROCESS FOR THE PREPARATION OF THE ENANTIOMERS OF 2-(2-FLUORO-4-BIPHENYL)PROPIONIC ACID

The present invention relates to a process for the preparation of 2-(2-fluoro-4-biphenyl)propionic acid enantiomers and, more particularly, it relates to a process for the preparation of (R) or (S)-2-(2-fluoro-4-biphenyl)propionic acid by resolution of derivatives of the corresponding amides with 1-(4-methylthiophenyl)-2-amino-1,3-propanediol or derivatives thereof.

2-(2-Fluoro-4-biphenyl)propionic acid is a drug with analgesic and anti-inflammatory activity, better known under its International non-proprietary name Flurbiprofen (The Merck Index, XI ed., page 657, no. 4124).

In the last years, it has bee broadly described in the literature that the (S) enantiomer of Flurbiprofen, hereinafter referred to as (S)-Flurbiprofen, shows therapeutic advantages with respect to the racemate. In addition, more recently, in the International patent application WO 9204018 (PAZ Arzneimittelenwicklungsgesellschaft GmbH), it has been described that (S)-Flurbiprofen is endowed with anti-inflammatory properties and that the (R) enantiomer, hereinafter referred to as (R)-Flurbiprofen, is endowed with analgesic properties.

In the literature, several methods for the preparation of Flurbiprofen enantiomers are described. Among these, there are also some processes including the resolution of diastereoisomeric salts.

The U.S. Pat. No. 4,209,638 (The Boots Company Limited) describes a process for increasing the proportion of a desired Flurbiprofen enantiomer by heating salts of Flurbiprofen with nitrogen organic bases (for example phenylethylamine) in a suitable solvent. The described process, in fact, is a process consisting in a II order resolution (or transformation) where the equilibrium between the two diastereoisomeric salts in solution is continuously shifted by the selective precipitation of one of the two salts up to obtaining the single diastereoisomeric salt with 100% theoretical yield (Enantiomers, Racemates and Resolutions—) J. Jacques, A. Collet and S. H. Wilen—edited by John Wiley & Sons 1981, Chapter 6, pages 369–377). However, the process conditions are extremely drastic (heating for some days at the reflux temperature) and do not allow to obtain an optically pure compound starting from the racemate, in any case.

The U.S. Pat. No. 4,973,745 (Medice Chem.-Pharm. Fabrik Puetter GmbH & Co. KG) describes the resolution of enantiomers of Flurbiprofen as diastereoisomeric salts obtained by mixing racemic Flurbiprofen with an optically pure form of threo-1-(4-nitrophenyl)-2-amino-1,3-propanediol.

The described operative conditions do not include a II order resolution and, also in this case, the desired enantiomer is obtained in a pure form only after repeated crystallizations.

The U.S. Pat. No. 4,983,765 (PAZ Arzneimittelenwicklungsgesellschaft GbmH) describes the separation of the enantiomers of Flurbiprofen by resolution of diastereoisomeric salts by using phenylethylamine as resolving agent.

Even if the desired enantiomer is obtained with high optical purity, the resolution yield is rather low since this is not a II order resolution.

In the European patent applications no. 0143371 and no. 0182279 (both in the name of Alfa Chemicals Italiana S.p.A.) processes for the preparation of (S)-2-(6-methoxy-2-naphthyl)propionic acid (Naproxen) by a II order resolution of the pair of diastereoisomeric amides obtained by reacting the racemic acid with a β-aminoalcohol, in particular S(+)-2-aminobutanol, have been described.

Afterwards, in a paper published by Slegel et al. in Journal of Pharmaceutical & Biomedical Analysis, Vol. 5, No. 7, pages 665–673, 1987, it is reported that the amides of some arylalkanoic acids, such as Naproxen and Fenoprofen, with 1-(4-nitrophenyl)-2-amino-1,3-propanediol can be used for the enantiomeric separation of said acids by thin layer chromatography (TLC).

We have now found that, by transforming racemic Flurbiprofen into the amide of a suitable derivative of threo-1-(4-methylthiophenyl)-2-amino-1,3-propanediol, the resultant diastereoisomeric mixture can be separated by a II order resolution.

Therefore, object of the present invention is a process for the preparation of 2-(2-fluoro-4-biphenyl)propionic acid enantiomers which comprises (a) the reaction of 2-(2-fluoro-4-biphenyl)propionic acid or a derivative thereof of fornula

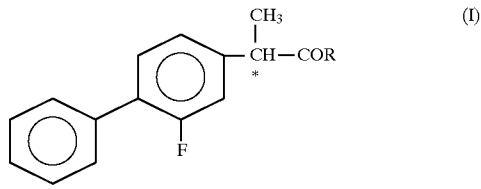

wherein R is a $C_1$–$C_4$ alkoxy group or a chlorine or bromine atom and the asterisk shows the chiral carbon atom;

with an optically pure stereoisomer of threo 1-(4-methylthiophenyl)-2-amino-1,3-propanediol or a derivative thereof of formula

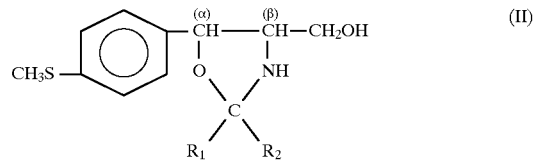

wherein $R_1$ and $R_2$, the same each other, are a hydrogen atom, a $C_1$–$C_3$ alkyl group or, together with the carbon atom to which they are bonded, form a $C_5$–$C_6$ cycloalkyl group; the asymmetric carbon atoms marked by α and β have both R or S configuration;

(b) the transformation of the diastereoisomeric mixture of the resultant amides into the corresponding mixture of ketals of fornula

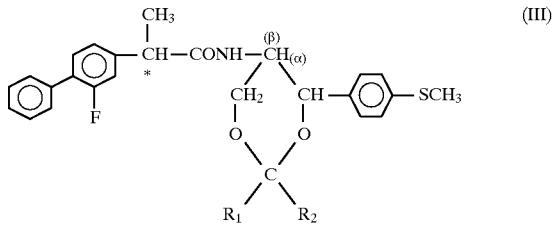

wherein $R_1$ and $R_2$ have the already reported meanings; the asterisk shows the chiral carbon atom and the asymmetric carbon atoms marked by α and β have both R or S configuration;

(c) the preferential crystallization of one of the two diastereoisomers of the ketals of formula (III) and the contemporaneous epimerization to the carbon atom marked by an asterisk by heating the mixture of the two diastereoisomers of formula (III) in the presence of equimolar amounts of an alkali metal $C_1$–$C_4$ alkoxide in a $C_1$–$C4$ alcoholic solvent;

(d) the acid hydrolysis of the resultant diastereoisomeric pure ketal to obtain the corresponding 2-(2-fluoro-4-biphenyl)propionic acid enantiomer in optically pure form.

The process object of the present invention consists of a II order resolution of the diastereoisomeric mixture of ketals of formula (III) and allows to obtain the Flurbiprofen enantiomers in optically pure form.

In fact, the characterizing feature of the present process is represented by the epimerization in solution of the mixture of ketals of formula (III) with the contemporaneous preferential crystallization of one of the two diastereoisomeric ketals present in solution.

It is evident that the epimerization reaction involves selectively the chiral carbon atom marked by an asterisk, that is the carbon atom deriving from 2-(2-fluoro-4-biphenyl)propionic acid. The contemporaneity of the epimerization and of the preferential crystallization allows to obtain the desired diastereoisomeric ketal, and consequently the corresponding Flurbiprofen enantiomer, with 100% theoretical yield contrary to the 50% theoreical yield of conventional resolutions.

Furthermore, it is evident that by changing the configuration of threo 1-(4-methylthiophenyl)-2-amino-1,3-propanediol, hereinafter referred to as Thiomicamine, or of its derivative of formula (II) used in step (a) of the process object of the present invention, it is possible to select which Flurbiprofen enantiomer will be obtained after hydrolysis.

For example, starting from threo Thiomicamine, or from a derivative thereof of formula (II), with (S,S) configuration and working in a suitable alcoholic solvent, the precipitation of the ketal of formula (III) with (S,S,S) configuration and, consequently, after hydrolysis, (S)-Flurbirprofen will be obtained.

By using the same alcoholic solvent but starting from threo Thiomicamine, or from a derivative thereof of formula (II), with (R,R) configuration, the precipitation of the ketal of formula (III) with (R,R,R) configuration and consequently, after hydrolysis, (R)-Flurbiprofen will be obtained, in the same way.

The parameters and the characterizing aspects of each step of the process object of the present invention are now discussed.

Step (a)

This step consists of the reaction of 2-(2-fluoro-4-biphenyl)propionic acid or a derivative thereof of formula

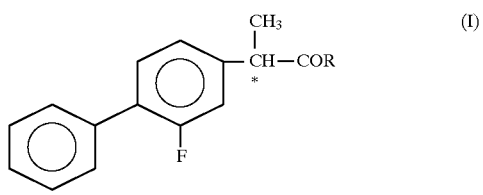

wherein R is a $C_1$–$C_4$ alkoxy group or a chlorine or bromine atom;

with an optically pure stereoisomer of threo Thiomicamine or a derivative thereof of formula

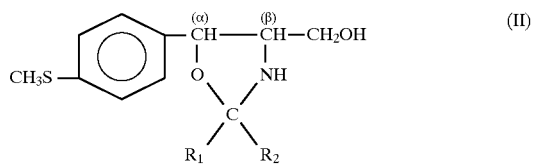

wherein $R_1$ and $R_2$, the same each other, are a hydrogen atom, a $C_1$–$C_3$ alkyl group or, together with the carbon atom to which they are bonded, form a $C_5$–$C_6$ cycloalkyl group; the asymmetric carbon atoms marked by α and β have bath R or S configuration.

The starting compound can be a racemic mixture of 2-(2-fluoro-4-biphenyl)propionic acid (Flurbiprofen) or a derivative thereof of formula (I) as well as a mixture enriched in one of the two enantiomers.

Preferably, the starting compound as racemic mixture is used.

The optional derivative of formula (I) is prepared starting from 2-(2-fluoro-4-biphenyl)propionic acid itself by conventional methods for the preparation of esters or of acyl halides.

Preferably, a derivative of formula (I) wherein R is a chlorine atom or a methoxy or butoxy group is used as starting compound.

The derivative of formula (I) wherein R is a chlorine atom can be advantageously prepared in situ from 2-(2-fluoro-4-biphenyl)propionic acid by reaction, for example, with thionyl chloride in a suitable solvent and in the presence of catalytic amounts of N,N-dimethylfonnamide.

Also the derivative of formula (I) wherein R is a methoxy or butoxy group can be advantageously prepared in situ by reaction with the corresponding alcohol in the presence of a catalytic amount of a mineral acid, for example sulfuric acid, in a suitable solvent.

The resultant derivative of formula (I) can be reacted directly with threo Thiomicamine or a derivative thereof of formula (II) without isolation or purification.

Preferably, threo Thiomicamine is used.

As already reported, both the enantiomers of threo Thiomicamine or of its derivatives of formula (II), that is both the enantiomer having (S,S) configuration and the enantiomer having (R,R) configuration, can be used. The selection of the enantiomer to be used will depend on the Flurbiprofen enantiomer it is desired to obtained.

The reaction with threo Thiomicamine or a derivative thereof of formula (II) is carried out according to conventional techniques for the preparation of amides.

For example, by using an ester of formula (I) (R=$C_1$–$C_4$ alkoxy) as starting compound, the reaction is carried out by heating in a suitable solvent in the presence of a catalytic amount of an alkali metal $C_1$–$C_4$ alkoxide in a $C_1$–$C_4$ alcoholic solvent.

Specific examples of alkali metal $C_1$–$C_4$ alkoxides are sodium methoxide, sodium ethoxide, sodium n.butoxide and potassium t.butoxide.

Specific examples of $C_1$–$C_4$ alcoholic solvents are methanol, ethanol, propanol, isopropanol, 1-butanol, 2-butanol, 1-hydroxy-2-methylpropane and 1-hydroxy-1,1-dimethylethane.

Preferably, sodium methoxide in methanol is used.

Otherwise, by using an acyl halide of formula (I) (R=chlorine or bromine), the reaction with Thiomicamine is carried out in the presence of a tertiary amine, preferably triethylamine, in a suitable organic solvent.

Thus, starting from Flurbiprofen or from a racemic mixture of a derivative of formula (I), by reaction with an enantiomer of threo Thiomicamine or a derivative thereof (II) according to what above reported, a substantially 1:1 mixture of the two corresponding diastereoisomeric amides of Flurbiprofen is obtained.

Threo Thiomicamine and the oxazolidines of formula (II) are known compounds, described for example in the European patent application no. 0130633 (Zambon S.p.A.).

Step (b)

This step consists of the transformation of the diastereoisometric mixture of the amides obtained in the preceding step into the corresponding mixture of ketals of formula

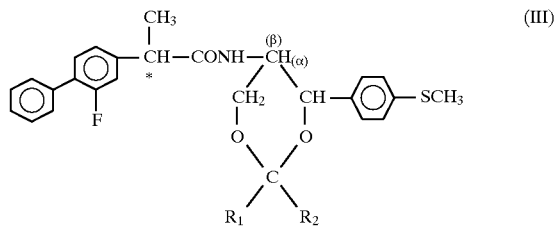

wherein $R_1$ and $R_2$, the same each other, are a hydrogen atom, a $C_1$–$C_3$ alkyl group or, together with the carbon atom to which they are bonded, form a $C_5$–$C_6$ cycloalkyl group; the asterisk shows the chiral carbon atom and the carbon atoms marked by α and β have both R or S configuration.

The transformation is carried out according to conventional methods for ketalization or opening of the oxazolidine ring followed by ketalization.

In fact, in the case of amides obtained by reaction with threo Thiomicamine, the transformation into the corresponding ketals of formula (III) will be carried out by direct ketalization, for example by reaction with a ketone of formula $R_1COR_2$ wherein $R_1$ and $R_2$ have the above reported meanings.

Such a reaction is carried out by conventional ketalization techniques, for example by using a catalytic amount of a mineral acid and in the presence of a dehydrating agent or under other usual conditions for removing water (azeotropic distillation).

Preferably, the ketalization reaction is carried out in the presence of triethylorthoformate and of catalytic amounts of sulfuric acid.

Still more preferably, acetone is used as ketalizing agent so obtaining the ketals of formula (II) wherein $R_1$ and $R_2$ are methyl groups.

In the case of amides obtained by reaction with a derivative of threo Thiomicamine of formula (II), the transformation into the corresponding ketals of formula (III) can be carried out by opening the oxazolidine ring and subsequent ketalization carried out in a single step by simple treatment with acids.

The ketals of formula (III) are new compounds and they are a further object of the present invention.

Preferred compounds of formula (III) are the compounds wherein $R_1$ and $R_2$, the same each other, are methyl groups.

Furthermore, the compounds of formula (III) are one of the characterizing features of the process object of the present invention.

Their peculiarity is demonstrated by the fact that they represent, as far as we know, the sole example of amides of Flurbiprofen which give rise to a II order resolution according to the present invention.

In fact, our attempts to carry out the II order resolution on the diastereoisomeric mixture of unketalized amides obtained by direct reaction with threo Thiomicamine or on the amides obtained by reaction with a β-aminoalcohol, such as for example 2-aminobutanol, according to what described for the resolution of Naproxen in the already cited European patent applications no. 0143371 and no. 0182279, did not lead in any case to obtain a product with a significant increase of the diastereoisomeric purity.

Step(c)

This step consists of the preferential crystallization of one of the two diastereoisomers of the ketals of formula (III) and of the contemporaneous epimerization to the carbon atom marked by an asterisk by heating the mixture of the two diastereoisomers of formula (III) in the presence of equimolar amounts of an alkali metal $C_1$–$C_4$ alkoxide in a $C_1$–$C_4$ alcoholic solvent.

As already underlined, this step consists of a II order resolution and represents the characterizing feature of the overall process for the preparation of the Flurbiprofen enantiomers according to the invention.

As such, therefore, it is a preferred object of the present invention.

The peculiarity of this step consists of the fact that, in addition to a preferential crystallization of one of the two diastereoisomers of the ketal of formula (III), there is also an epimerization in situ so that the theoretical yield of desired diastereoisomer is equal to 100%, calculated on the base of the total amount of the two diastereoisomers present in the starting mixture, It is worth underlining that the epimerization occurs in situ that in the same crystallization environment.

From a practical point of view, this allows a remarkable advantage since it means that the preferential crystallization and the epimerization occurs contemporaneously and the resultant and eventually isolated product is exclusively the desired diastereoisomer.

Practically, in fact, the yield of the II order resolution according to the present invention is always higher than 75–80%.

Specific examples of alkali metal $C_1$–$C_4$ alkoxides are sodium methoxide, sodium ethoxide, sodium n.butoxide and potassium t.butoxide.

Specific examples of $C_1$–$C_4$ alcoholic solvents are methanol, ethanol, propanol, isoprepanol, 1-butanol, 2-butanol, 1-hydroxy-2-methylpropane and 1-hydroxy-1,1-dimethylethane. Preferably, sodium methoxide (in the form of a methanolic solution) in isopropanol is used. A preferred embodiment of the step of preferential crystallization and of epimerization according to the invention is the following.

An equimolar amount of sodium methoxide in methanolic solution is added at warm to a solution containing a 1:1 mixture of the diastereoisomeric ketals of formula (III) wherein $R_1$ and $R_2$ are methyl groups. After keeping at warm for some hours, the solution is slowly cooled in some hours up to room temperature.

During the cooling phase the spontaneous precipitation of a pure diastereoisomer of the ketal of formula (III), which is isolated by filtration, is observed.

Step (d)

This step consists of the acid hydrolysis of the diastereoisomeric pure ketal of fornula (III) in order to obtain the corresponding 2-(2-fluoro-4-biphenyl)propionic acid enantiomer in optically pure form.

The acid hydrolysis is carried out by treatment at warm with a concentrated mineral acid in a suitable solvent.

Preferably, the hydrolysis is carried out with concentrated hydrochloric acid in hot acetic acid. Still more preferably, the hydrolysis is carried out with 3–5M hydrochloric acid in acetic acid at temperatures from 50° C. to 75° C.

It is worth underlining that the conditions of hydrolysis according to the process object of the present invention allow to obtain the desired Flurbiprofen enantiomer with the same enantiomeric purity of the ketal of formula (III) obtained by resolution according to the preceding step.

This is of extreme importance from a practical point of view because it is known that, often, the conditions under which a hydrolysis is carried out are also racemizing conditions with consequent total or partial loss of the optical purity of the final product.

The process object of the present invention has several advantages useful from the industrial point of view.

Such advantages, which have been already underlined, are represented in particular by the high yields, the easy industrial applicability and by the versatility.

The process object of the present invention so differs from the other known processes for the resolution of the Flurbiprofen enantiomers.

In particular, the high yields and the easy industrial applicability are due for the highest extent to the operative conditions under which step (c) is carried out.

In fact, as already underlined, the epimerization occurs in situ, that is in the same crystallization environment.

From a practical point of view, this implies a remarkable advantage because it means that the preferential crystallization and the epimerization occur contemporaneously and the resultant and eventually isolated product is exclusively the desired diastereoisomer in pure form with a 100% theoretical yield.

Furthermore the hydrolysis of the diastereoisomerically pure compound of formula (III) yields the Flurbiprofen enantiomer already in optically pure form without requiring further purifications.

In order to better illustrate the present invention the follow examples are now given.

EXAMPLE 1

Preparation of (RS)-2-(2-fluoro-4-biphenyl)propionic acid methyl ester

In a 250 cm$^3$ reactor, equipped with magnetic stirrer, thermometer and reflux florentine flask, toluene (78 g), (RS-2-(2-fluoro-4-biphenyl)propionic acid (100 g; 0.41 moles), methanol (66 g) and 96% sulfuric acid (1 g; 0.01 moles) were charged at room temperature, under nitrogen atmosphere.

The mixture was brought to the reflux temperature of methanol for about 3 hours, then cooled at room temperature. After basification with NaOH 5%, the phases were separated. The organic phase was neutralized with demineralized water (200 g).

After evaporation to residue under vacuum, the resultant thick oil was taken up at warm (50°–60ßC.) with isopropanol (40 g).

By cooling at room temperature the formation of a precipitate, which was dried in oven under vacuum at 45° C. overnight, was obtained affording (RS)-2-(2-fluoro-4-biphenyl)propionic acid methyl ester (68 g; 64% yield).

m.p. 50°–52° C.; $^1$H-NMR (CDCl$_3$, 300 MHz); δ (ppm); 1.53 (d, 3H, J=7.2 Hz); 3.70 (s, 3H); 3.75 (q, 1H, J=7.2 Hz); 7.10–7.60 (m, 8H).

EXAMPLE 2

Preparation of N-[(2S ,3S)-2-[1,3-dihyroxy-3-(4-methylthiophenyl)propyl]-2(RS)-(2-fluoro-4-biphenyl) propionamide In a 250 cm$^3$ reactor, equipped with magnetic stirrer, thermometer and reflux florentine flask, toluene (150 g), (RS)-2-(2-fluoro-4biphenyl)propionic acid methyl ester (50 g; 0.19 moles), prepared as described in example 1, (1S,2S) -1-(4-methylthiophenyl)-2-amino-1,3-propanediol (48.6 g) and sodium methoxide in 30% methanol (7 g; 0.038 moles) were charged at room temperature, under nitrogen atmosphere.

The reaction mass was brought to 85° C. for 5 hours while distilling methanol and, after this period, cooled at room temperature and then poured into demineralized water (300 g).

After acidification with H$_2$SO$_4$ 96% and separation of the phases, the organic phase was taken up with further demineralized water (100 g) and evaporated to residue under vacuum. The resultant crude N-[(2S,3S)-2-[1,3-dihydroxy-3-(4-methylthiophenyl)propyl]-2(RS)-(2-fluoro-4-biphenyl) propionamide (207 g) was used as such without further purifications in the next step.

EXAMPLE 3

Preparation of N-[(2S,3S)-2-[1,3-dihydroxy-3-(4-methylthiophenyl)propyl]-2(RS)-(2-fluoro-4-biphenyl) propionamide In a 250 cm$^3$ reactor, equipped with magnetic stirrer, thermometer and reflux condenser, methylene chloride (78 g), N,N-dimethylformamide (0.38 g; 0.005 moles) and (RS) -2-(2-fluoro-4-biphenyl)propionic acid (40 g; 0.16 moles) were charged at room temperature, under nitrogen atmosphere.

At the same temperature, thionyl chloride (21.4 g; 0.18 moles) was added in about 15 minutes. After 3.5 hours, the solvent and the volatile residues were removed under reduced pressure. The resultant oil residue was taken up with methylene chloride (78 g) (Solution A).

In a second anhydrous 500 cm$^3$ reactor, equipped with magnetic stirrer, thermometer and dropping funnel containing Solution A, methylene chloride (47 g), triethylamine (24.8 g; 0.25 moles) and (1S,2S)-1-(4-methylthiophenyl)-2-amino-1,3-propanediol (35 g; 0.16 moles) were charged at room temperature under nitrogen atmosphere.

The mixture was cooled at 15° C. and Solution A was added dropwise in about 60 minutes. After about 30 minutes, demineralized water (200 g) and 5M hydrochloric acid (25 g) were added, at the same temperature.

The phases were separated and the aqueous phase was taken up with methylene chloride (40 g).

The collected organic phases were neutralized with a 8% aqueous solution of sodium bicarbonate (50 g) and then brought to residue under vacuum obtaining crude N-[(2S,3S)2-[1,3-dihydroxy-3-(4-methylthiophenyl)propyl]-2(RS)- (2-fluoro-4-biphenyl)propionamide (74.3 g) which was used without further purifications in the next step.

A pure analytic sample was characterized by m.p. and $^1$H-NMR.

m.p. 112°–116° C.; $^1$H-NMR (CDCl$_3$+D$_2$O, 300 MHz): δ (ppm); 1.4 (d, 3H, J=7.1); 2.3 (s, 3H); 3.5 (q, 1H, J=7.1); 3.72 (dd, 1H, J=11.2 J=4.9); 3.77 (dd, 1H, J=11.2 J=5.25); 4.04 (dddd, 1H, J=8.18 J=4.9 J=5.25 J=3.05); 4.93 (d, 1H, J=3.05); 6.2 (d, 1H, J=8.18); 6.9–7.6 (m, 12H).

EXAMPLE 4

Preparation of N-[(2S,3S)-2-[1,3-dihydroxy-3-(4-methylthiophenyl)propyl]-2(RS)-(2-fluoro-4-biphenyl) propionamide In a 250 cm$^3$ reactor, equipped with magnetic stirrer, thermometer and reflux florentine flask, toluene (100 g), n.butanol (9.1 g; 0.123 moles), (RS)-2-(2-fluoro-4-biphenyl) propionic acid (20 g; 0.082 moles) and 96% sulfuric acid (0.42 g; 0.0041 moles) were charged at room temperature, under nitrogen atmosphere.

The reaction was was brought to 115° C. for 1.5 hours while distilling about 2 ml of water. At the end of the reaction, the solvent (25 ml) was distilled at atmospheric pressure so having toluene as the only reaction solvent.

After cooling to 15° C., 30% sodium methoxide in methanol (3.68 g; 0.094 moles) and (1S,2S)-1-(4- methylthiophenyl)-2-amino-1,3-propanediol (19.2 g; 0.094 moles) were added.

The mixture was brought under reflux (110° C.) for 3.5 hours isolating crude N-[(2S,3S)-2-[1,3-dihydroxy-3-(4-methylthiophenyl)propyl[-2(RS)-(2-fluoro-4-biphenyl) propionamide according to the procedure described in example 2.

EXAMPLE 5
Preparation of (4S,5S)-2,2-dimethyl-4-(4-methylthiophenyl)-5-N-[(2RS)-2-(2-fluoro-4-biphenyl) propionamide]-1,3-dioxane In a 500 cm³ reactor, equipped with magnetic stirrer, thermometer and reflux condenser, acetone (230 g), crude N-[(2S,3S)-2-[1,3-dihydroxy-3-(4-methylthiophenyl) propyl]-2(RS)-(2-fluoro-4-biphenyl)propionamide (83.4 g; 0.19 moles), prepared as described in example 2, 3 or 4, and 96% sulfuric acid (1 g; 0.01 moles) and, subsequently, at the same temperature in about 30 minutes triethylorthoformate (70.3 g; 0.47 moles) were charged at room temperature, under nitrogen atmosphere.

After about 14 hours under stirring the volatile residues were removed under vacuum and the oily residue was taken up with toluene (500 g).

Then, 8% sodium bicarbonate (30 g) and demineralized water (100 g) were added. The phases were separated by taking up the organic phase with demineralized water (100 g). The resultant organic solution was brought to residue under vacuum obtaining crude (4S,5S)-2,2-dimethyl-4-(4-methylthiophenyl)-5-N-[(2RS)-2-(2-fluoro-4-biphenyl) propionamide]-1,3-dioxane (95 g) which was used in the subsequent step without further purification.

EXAMPLE 6
Preparation of (4S,5S)-2,2dimethyl-4-(4-methylythiophenyl)-5-N-[(2S)-2-(2-fluoro-4-biphenyl) propionamide]-1,3-dioxane In a 500 cm³ reactor, equipped with magnetic stirrer, thermometer, reflux condenser and dropping funnel, isopropanol (39 g) and crude (4S,5S)-2,2-dimethyl-4-(4-methylthiophenyl)-5-N-[(2RS)-2-(2-fluoro-4-biphenyl) propionamide]-1,3-dioxane (114 g), prepared as described in example 5, were charged at room temperature, under nitrogen atmosphere.

The heterogeneous mass was heated under stirring at 70° C. obtaining a solution.

At this temperature 30% sodium methoxide in methanol (4.5 g) was added.

The reaction mixture was kept at this temperature for 2 hours and then cooled in about 3 hours up to about 55° C.

At this temperature the spontaneous precipitation began and the cooling was then continued at about 6° C./hour.

As soon as the temperature of 5° C. was reached, demineralized water (1 g) was added and the temperature was brought up to 20° C.

The precipitate was filtered and taken up with isopropanol (2×4 g).

After drying in oven under vacuum at 60° C. overnight (4S,5S)-2,2-dimethyl-4-(4-methylthiophenyl)-5-N-[(2S)-2-(2-fluoro-4-biphenyl)propionamide]-1,3-dioxane (8.8 g; 76% yield calculated by assuming as equal to 100% the titre of the starting racemic crude) was obtained.

m.p. 132–137° C.; $[\alpha]_D^{25}=+104°$ (c=1.0; CHCl$_3$); $^1$H-NMR (CDCl$_3$, 300 MHz): 1.34 (d, 3H, J=7.16); 1.43 (s, 3H); 1.51 (s, 3H, J=7.1); 2.3 (s, 3H); 3.44 (q, 1H, J=7.16); 3.83 (dd, 1H, J=12.21 J=1.87); 4.19 (ddd, 1H, J=9.24 J=1.68 J=1.68 J=1.87); 4.21 (dd, 1H, J=12.21 J=1.68); 5.08 (d, 1H, J=1.68); 6.03 (d, 1H, J=9.24); 6.7–7.6 (m, 12H).

EXAMPLE 7
Preparation of 2(S)-(2-fluoro-4-biphenyl)propionic acid

In a 100 cm³ reactor, equipped with magnetic stirrer, thermometer and reflux condenser, glacial acetic acid (10.5 g), 5M hydrochloric acid (14 g; 0.063 moles) and (4S,5S)-2,2-dimethyl-4-(4-methylthiophenyl)-5-N-[(2S)-2-(2-fluoro-4-biphenyl)propionamide]-1,3-dioxane (10 g; 0.021 moles), prepared as described in example 6, were charged at room temperature, under nitrogen atmosphere.

The heterogeneous mass was heated under stirring at 70° C. for 2 hours obtaining a limpid homogeneous solution.

After cooling at about 30° C. a little seed of optically pure 2(S)-(2-fluoro-4-biphenyl)propionic acid was added. After precipitation, the cooling was continued up to 15° C., the solid was filtered and washed with demineralized water (3×10 g).

The resultant wet solid was dried in oven under vacuum at 55° C. for 6 hours obtaining 2 (S)-(2-fluoro-4-biphenyl) propionic acid (3.56 g; 65% yield calculated by assuming as equal to 100% the titre of the starting compound).

HPLC titre 94% (purity 99%).

e.e. (HPLC) 98%

$[\alpha]_D^{25}=+44.6°$ (c=1.03; CHCl$_3$).

What we claim is:
1. A process for the preparation of 2-(2-fluoro-4-biphenyl) propionic acid enantiomers which comprises

(a) the reaction of 2-(2-fluoro-4-biphenyl)propionic acid or a derivative thereof of formula

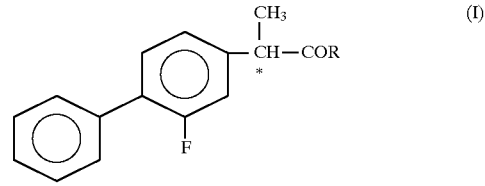

wherein R is a $C_1$–$C_4$ alkoxy group or a chlorine or bromine atom and the asterisk shows the chiral carbon atom;

with an optically pure stereoisomer of threo 1-(4-methylthiophenyl)-2-amino-1,3-propanediol or a derivative thereof of formula

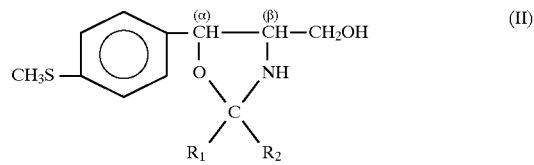

wherein $R_1$ and $R_2$ are both a hydrogen atom, a $C_1$–$C_3$ alkyl group or, together with the carbon atom to which they are bonded, form a $C_5$–$C_6$ cycloalkyl group; the asymmetric carbon atoms marked by α and β have both R or S configuration;

(b) the transfomation of the diastereoisomeric mixture of the resultant amides into the corresponding mixture of ketals of formula

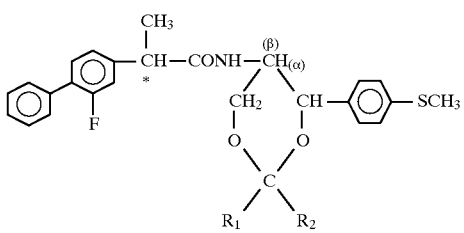

wherein $R_1$ and $R_2$ have the already reported meanings; the asterisk shows the chiral carbon atom and the asymmetric carbon atoms marked by α and β have both R or S configuration;

(c) the crystallization of one of the two diastereoisomers of the ketals of formula (III) and the contemporaneous epimerization to the carbon atom marked by an asterisk by heating the mixture of the two diastereoisomers of formula (III) in the presence of equimolar amounts of an alkali metal $C_1$–$C_4$ alkoxide in a $C_1$–$C_4$ alcoholic solvent;

(d) the acid hydrolysis of the resultant diastereoisomeric pure ketal to obtain the corresponding 2-(2-fluoro-4-biphenyl)propionic acid enantiomer in optically pure form.

2. A process according to claim 1 wherein step (a) is carried out starting from 2-(2-fluoro-4-biphenyl)propionic acid or from a compound of formula (I) in the form of racemic mixture.

3. A process according to claim 1 wherein step (a) is carried out starting from a compound of formula (I) wherein R is a chlorine atom or a methoxy or butoxy group.

4. A process according to claim 1 wherein, in step (a), an optically pure stereoisomer of threo 1-(4-methylthiophenyl)-2-amino-1,3-propanediol is used.

5. A process according to claim 1 wherein, in step (c), a ketal of formula (III) wherein $R_1$ and $R_2$ are both methyl groups is used.

6. A process according to claim 1 wherein, in step (c), the alkali metal $C_1$–$C_4$ alkoxide is selected among sodium methoxide, sodium ethoxide, sodium n.butoxide and potassium t.butoxide.

7. A process according to claim 1 wherein, in step (c), the $C_1$–$C_4$ alcoholic solvent is selected among methanol, ethanol, propanol, isopropanol, 1-butanol, 2-butanol, 1-hydroxy-2-methylpropane and 1-hydroxy-1,1-dimethylethane.

8. A process according to claim 1 wherein, in step (c), sodium methoxide in isopropanol is used.

9. A process according to claim 1 wherein, in step (d), the hydrolysis is carried out with concentrated hydrochloric acid in warm acetic acid.

10. A process for the preparation of 2-(2-fluoro-4-biphenyl)propionic acid enantiomers which comprises the crystallization of one of the two diastereoisomers of the ketals of formula

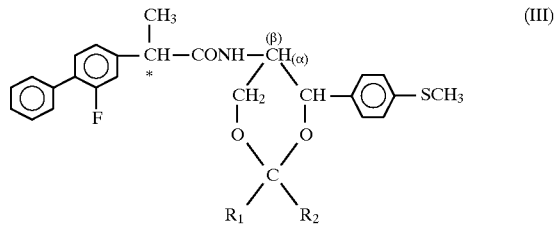

wherein $R_1$ and $R_2$ are both a hydrogen atom, a $C_1$–$C_3$ alkyl group or, together with the carbon atom to which they are bonded, form a $C_5$–$C_6$ cycloalkyl group; the asterisk shows the chiral carbon atom and the asymmetric carbon atoms marked by α and β have both R or S configuration;

and the contemporaneous epimerization to the carbon atom marked by an asterisk by heating the mixture of the two diastereoisomers of formula (III) in the presence of equimolar amounts of an alkali metal $C_1$–$C_4$ alkoxide in a $C_1$–$C_4$ alcoholic solvent.

11. A process according to claim 10 wherein a ketal of formula (III) wherein $R_1$ and $R_2$ are methyl groups.

12. A process according to claim 10 wherein the alkali metal $C_1$–$C_4$ alkoxide is selected among sodium methoxide, sodium ethoxide, sodium n.butoxide and potassium t.butoxide.

13. A process according to claim 10 wherein the $C_1$–$C_4$ alcoholic solvent is selected among methanol, ethanol, propanol, isopropanol, 1-butanol, 2-butanol, 1-hydroxy-2-methylpropane and 1-hydroxy-1,1-dimethylethane.

14. A process according to claim 10 wherein sodium methoxide in isopropanol is used.

* * * * *